(12) United States Patent
Heidt et al.

(10) Patent No.: US 6,194,615 B1
(45) Date of Patent: Feb. 27, 2001

(54) CROSSLINKERS BASED ON DIBENZALACETONE DERIVATIVES

(75) Inventors: Philip Conrad Heidt, Kingsport, TN (US); Matthew Lynn Elliott, Gate City, VA (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/335,196

(22) Filed: Jun. 17, 1999

Related U.S. Application Data

(60) Provisional application No. 60/112,289, filed on Dec. 15, 1998.

(51) Int. Cl.$^7$ .................................................. C07C 211/00
(52) U.S. Cl. ..................... 564/384; 564/397; 564/446; 564/455; 564/134; 564/157; 564/152; 568/860; 525/55; 525/185; 525/390; 525/416; 525/452; 525/509; 525/523; 525/540

(58) Field of Search ................................ 564/384, 397, 564/446, 455, 134, 157, 152; 568/816; 525/55, 185, 390, 416, 452, 509, 523, 540

(56) References Cited

U.S. PATENT DOCUMENTS

| | | |
|---|---|---|
| 4,923,958 | 5/1990 | Blount et al. . |
| 4,965,399 | 10/1990 | Zoeller et al. . |
| 5,025,086 | 6/1991 | Blount, Jr. et al. . |

*Primary Examiner*—Samuel Barts
(74) *Attorney, Agent, or Firm*—Rose M. Allen; Harry J. Gwinnell

(57) ABSTRACT

The present invention relates to the composition, process of preparation, and use of novel derivatives prepared from 1,5-bis-(4'-carbomethoxyphenyl)-1,4-pentadien-3-one. These novel compositions can act as crosslinkers with polyfunctional monomeric, oligomeric, and/or polymeric anhydrides, esters, carboxylic acids, isocyantes, epoxies, carbonates, acetoacetates, and alkoxylated melamines.

18 Claims, No Drawings

CROSSLINKERS BASED ON DIBENZALACETONE DERIVATIVES

This invention claims the priorty of provisional application 60/112,289 filed Dec. 15, 1998.

Background of the Invention

Dibenzalacetone derivatives are typically prepared by the reaction of two molecules of a benzaldehyde derivative with one molecule of acetone usually under basic conditions. Aldol reactions of this type are known and specifically the reaction of methyl p-formylbenzoate with acetone to provide 1,5-bis-(4'-carbomethoxyphenyl)-1,4-pentadien-3-one has been previously described by Blount and Zoeller in U.S. Pat. Nos. 5,025,086, 4,965,399, and 4,923,958.

Hydrogenation of the dibenzalacetone backbone (the pentadienone unit) with either homogeneous or heterogeneous catalysts provides for a 3-pentanone or 3-pentanol structure which is now of particular interest for developing polyfunctional derivatives which can be useful in the preparation of coatings, particularly as crosslinkers. Only in U.S. Pat. No. 5,025,086 does Blount and Zoeller describe a hydrogenation process to prepare the cycloaliphatic derivatives of dibenzalacetone; more specifically 1,5-bis-(4'-carbomethoxycyclohexyl)-3-pentanol and 1,5-bis-(4'-carbomethoxycyclohexyl)-3-pentanone.

In the cited references, the uses of the dibenzalacetone derivatives were limited to incorporation into polyester resins with other polyols and polybasic acids commonly known in the art. These dibenzalacetone derivatives cited were not, however, further developed into polyfunctional derivatives which could be used directly as crosslinkers and the types of crosslinkers which could be useful as crosslinkers were not disclosed.

The trifunctional amine derivatives described in the present invention are particularly of interest since the commercial availability of trifunctional amines which contain only primary amines is quite limited. One such trifunctional primary amine is tris-(2-aminoethyl)amine, also refered to as TREN® amine, available from Pressure Chemical Company. This trifunctional amine is quite expensive for most applications used in coatings.

Another use of the dibenzalacetone derivatives described within are for the preparation of poly betahydroxyethylamides. Beta-hydroxyethylamides are known and used in the art, particularly in powder coatings. One such commercial product is Primid XL-552® crosslinker available from EMS-Chemie AG.

SUMMARY OF THE INVENTION

The present invention describes novel polyfunctional compounds prepared from dibenzalacetone derivatives useful as crosslinkers in coatings applications. The novel polyfunctional compounds include 1,5-bis-(4'-aminomethylcyclohexyl)-3-aminopentane; 1,5-bis-(4'-aminomethylphenyl)-3-aminopentane; 1,5-bis-(4'-hydroxymethylcyclohexyl)-3-pentanol; 1,5-bis-(4'-(bis-2-hydroxyethyl)carboxamidephenyl)-3-(bis-2-hydroxyethyl)aminopentane; and 1,5-bis-(4'-(bis-2-hydroxyethyl)carboxamidecyclohexyl)-3-(bis-2-hydroxyethyl)aminopentane. The scope of this invention covers the novel compounds, their process of preparation, and their use as crosslinkers, reactants and/or curing agents in coatings and related materials.

DETAILED DESCRIPTION OF THE INVENTION

The scope of this invention is intended to cover the composition, process of preparation, and use of novel dibenzalacetone derivatives. The method of preparation of these novel compositions is described further in the following paragraphs and the general synthetic pathway(s) shown below.

The general synthesis of 1,5-bis-(4'-carbomethoxyphenyl)-1,4-pentadien-3-one, 1, has been previously described by Blount and Zoeller in U.S. Pat. No. 5,025,086 and references cited within. Methyl p-formylbenzoate was purchased from Fluka Chemical Company and was used without any further purification. It is from methyl p-formylbenzoate and acetone, that all of the novel compositions described originate.

The synthetic pathway to prepare 1,5-bis-(4'-aminomethylcyclohexyl)-3-aminopentane, 5, can follow two paths. One such path involves the hydrogenation of 1,5-Bis-(4'-carbomethoxyphenyl)-1,4-pentadien-3-one, 1, to 1,5-bis-(4'-carbomethoxycyclohexyl)-3-pentanone, 7, followed by addition of anhydrous or aqueous ammonia at or near ambient to elevated temperatures to provide 1,5-bis-(4'-carboxamidecyclohexyl)-3-iminopentane, 9. The latter product is then reduced to provide the desired trifunctional amine, 5.; as shown below.

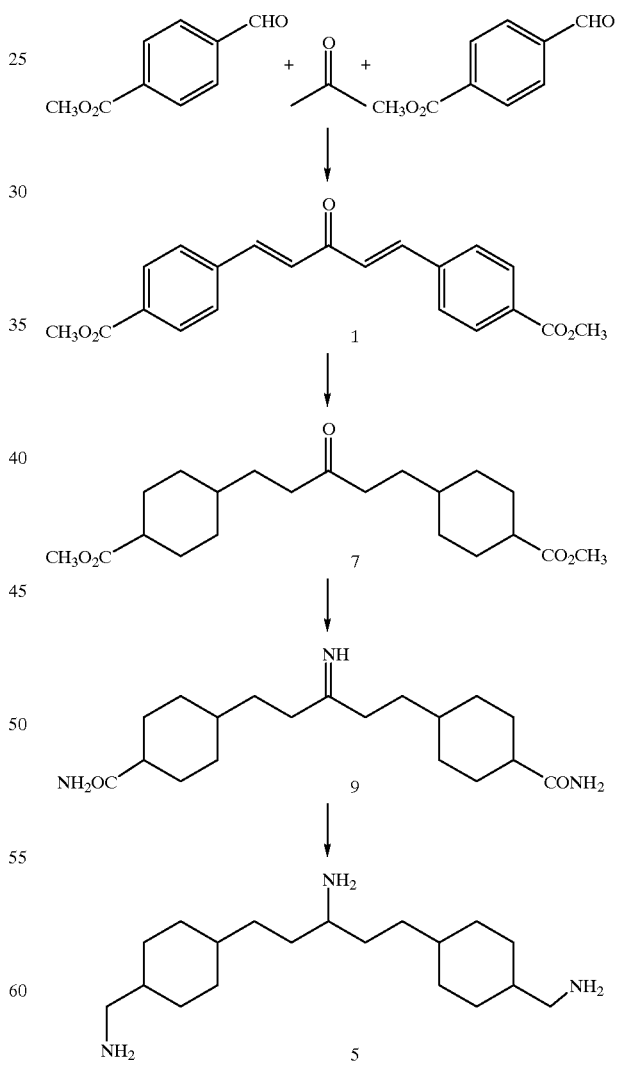

The second pathway involves the palladium on carbon hydrogenation of 1 to 1,5-bis-(4'-carbomethoxyphenyl)-3-pentanone, 2, followed by addition of anhydrous or aqueous ammonia at or near ambient to elevated temperatures to provide 1,5-bis-(4'-carboxamidephenyl)-3-iminopentane, 3. The latter product is then reduced to form 1,5-bis-(4'-aminomethylphenyl)-3-aminopentane, 4, a novel trifunctional amine. This amine can further be hydrogenated to form 5, another novel trifunctional amine described above.

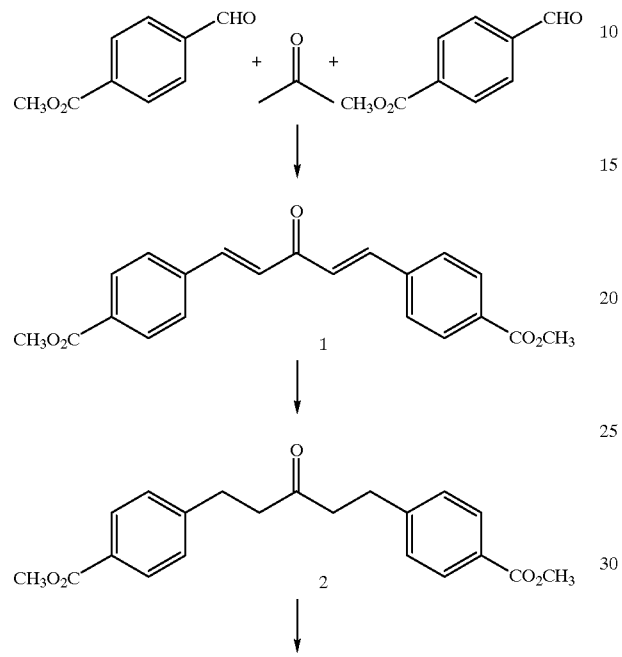

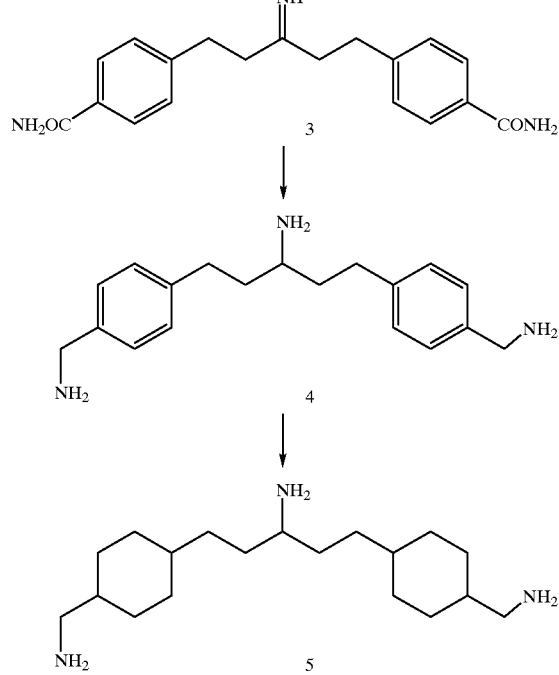

The synthetic pathway to prepare 1,5-bis-(4'-hydroxymethylcyclohexyl)-3-pentanol, 8, starts from 1 which is then reduced to form either 1,5-bis-(4'-carbomethoxycyclohexyl)-3-pentanol, 6, or 1,5-bis-(4'-carbomethoxycyclohexyl)-3-pentanone, 7, or a mixture of the two. Either or both of 6 and 7 is then reduced using hydride reagents such as lithium aluminum hydride to form the desired trihydroxyl compound, 8.

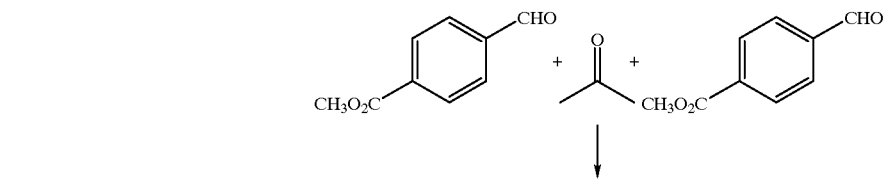

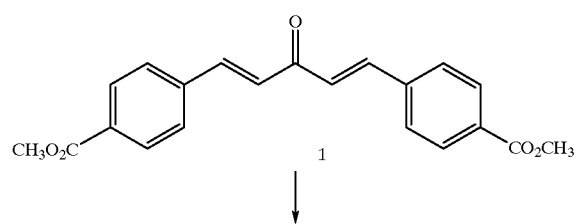

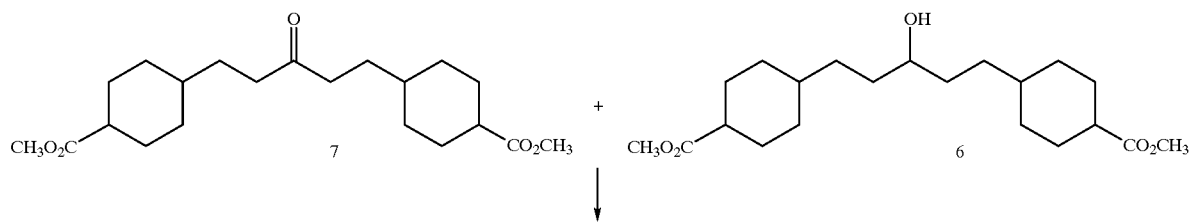

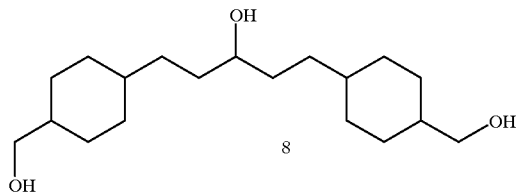

The 2-hydroxyethylamide compounds, 1,5-Bis-(4'-(bis-2-hydroxyethyl)carboxamidephenyl)-3-(bis-2-hydroxyethyl)aminopentane, 11, and 1,5-Bis-(4'-(bis-2-hydroxyethyl)carboxamidecyclohexyl)-3-(bis-2-hydroxyethyl)aminopentane, 12, originate from the dibenzalacetone derivative 1 as well. The aromatic-based 2-hydroxyethylamide derivative 11 follows the pathway of 2 previously described which is then treated with diethanolamine to form 1,5-bis-(4'-bis-(2-hydroxyethyl)carboxamidephenyl)-3-bis-(2-hydroxyethyl)amino-2-pentene, 10 which is then further reduced to form 11 or 12.

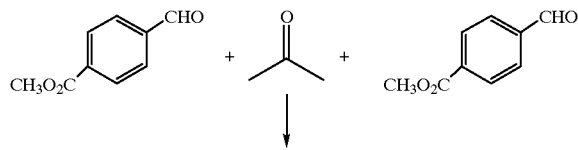

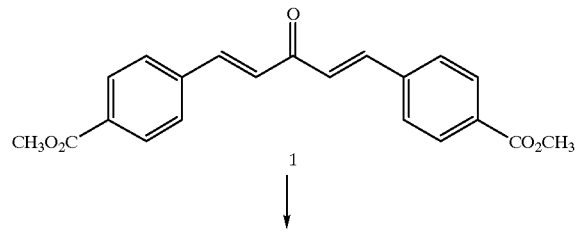

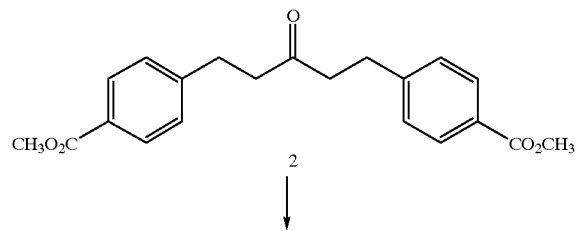

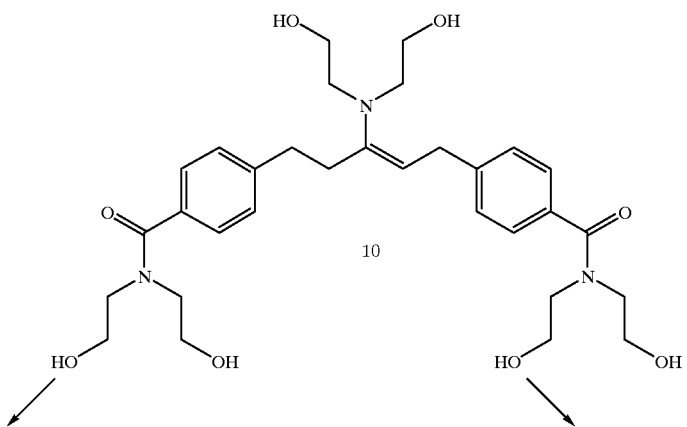

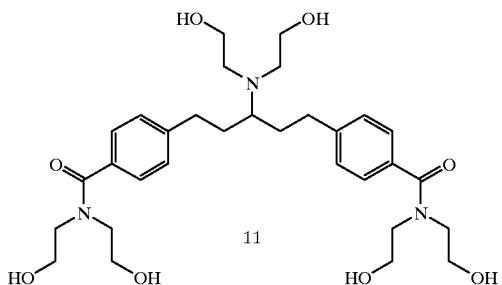
11

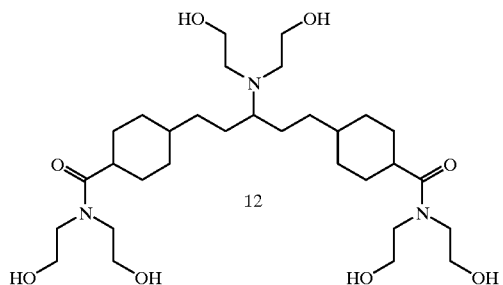
12

The cycloaliphatic-based 2-hydroxyethylamide, 12, may also follow the pathway through the keto-diester 1,5-Bis-(4'-carbomethoxycyclohexyl)-3-pentanone 7, which is treated with diethanolamine to give 13 which is then reduced to 12.

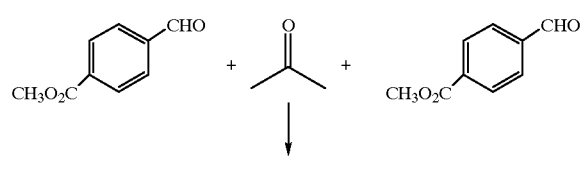

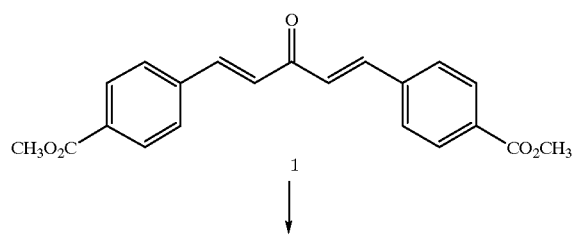
1

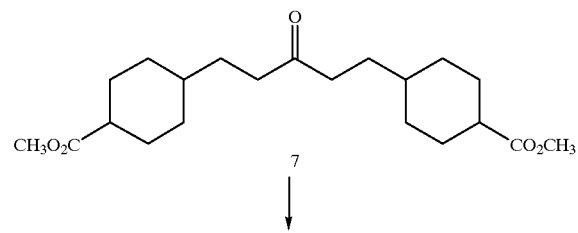
7

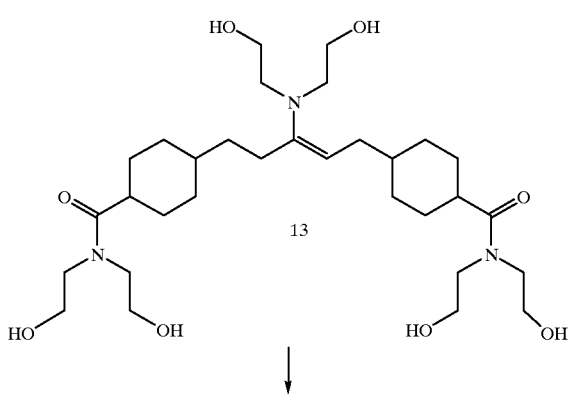
13

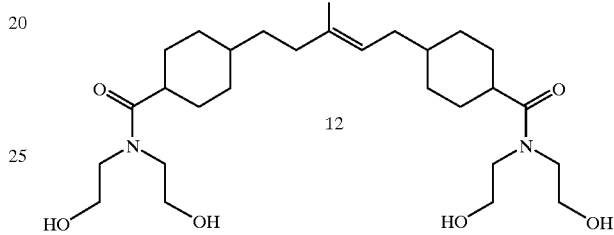
12

The trifunctional amines 4 and 5 may act as crosslinkers with polyfunctional monomeric, oligomeric, or polymeric forms of anhydrides, esters, carboxylic acids, isocyanates, carbonates, acetoacetates, alkoxylated melamines, or epoxies to form crosslinked networks of polyamides, ureas, urethanes, acetoacetamides, and the like. The triol, 8, may react with polyfunctional anhydrides, esters, and carboxylic acids to form polyesters; with polyfunctional isocyanates to form urethanes; with polyfunctional carbonates, acetoacetates, epoxies, and with alkoxylated melamines to form crosslinked networks.

The 2-hydroxylethylamides, 11 and 12 may react with polyfunctional esters, anhydrides, or carboxylic acids to form polyesters; polyfunctional isocyanates to form urethanes; and with epoxies, carbonates, acetoacetates, and alkoxylated melamines to form crosslinked networks.

Hydrogenation reactions can be accomplished in the presence of Group VIII metal catalysts such as ruthenium, rhodium, palladium, and platinum deposited on or supported by a catalyst support material such as silica, alumina, carbon, titania, etc. Depending on the selectivity, conversion, and other parameters required, the concentration of catalyst on the support material may differ widely. Additionally, other factors such as the rate of conversion and functional group selectivity can influence the type of catalyst used.

Generally, preferable hydrogenation conditions will be within the range of about 20° to 300° C. and about 50 to 3000 psig hydrogen. The more preferred ranges are about 150° to 250° C. and about 500 to 1500 psig hydrogen. Typically, the hydrogenation reactions are carried out in the presence of an inert organic solvent such as C6 to C12 aromatics, methanol and other alcohols to about 6 carbon atoms, and various esters such as methyl acetate, ethyl acetate, methyl butyrate and the like.

Another type of hydrogenation which is preferred uses copper chromite as a catalyst in an inert solvent. Other catalysts such as Raney nickel can give satisfactory results as well. Still, homogeneous catalysts such as Wilkinson's catalyst (chlorotris(triphenylphosphine)rhodium) are excellent hydrogenation catalysts, but sometimes find limited use on large industrial scale.

This invention can be further illustrated by the following examples of preferred embodiments thereof, although it will be understood that these examples are included merely for purposes of illustration and are not intended to limit the scope of the invention unless otherwise specifically indicated.

EXAMPLES

Example 1

1,5-Bis-(4'-carbomethoxyphenyl)-1,4-pentadien-3-one (1)

1,5-Bis-(4'-carbomethoxyphenyl)-1,4-pentadien-3-one, 1, was made by the process outlined in U.S. Pat. No. 5,025,086.

Example 2

1,5-Bis-(4'-carbomethoxyphenyl)-3-pentanone (2)

The procedure to obtain this material has been described earlier in U.S. Pat. No. 4,965,399 using a wide range of hydrogenation conditions. The material used throughout this application was prepared by the method outlined below.

To a 2-L 3-necked round-bottom flask equipped with a magnetic stir-bar was carefully added 1,5-bis-(4'-carbomethoxyphenyl)-1,4-pentadien-3-one (52.56 g, 0.15 moles), 5 pecent palladium on carbon (3.0 g), and THF (800 mL). The air was evacuated and the flask was refilled with hydrogen contained in two helium-quality balloon (ca. 4 L each). The evacuation procedure was repeated three times per balloon before the mixture was rapidly stirred at ambient temperature (ca. 25° C.). After stirring overnight, a sample was removed and filtered through a filtering aid and checked by FDMS. Within 24 hours, the full mixture was filtered through Dicalite® filtering aid (available from Aldrich Chemical Company) packed in a glass-fritted funnel, washed with THF, and concentrated in vacuo to provide a quantitative amount of white solids.

Example 3

1,5-Bis-(4'carboxamidephenyl)-3-iminopentane (3)

Route 1. A suspension of 1,5-bis-(4'-carbomethoxyphenyl)-3-pentanone (5.40 g, 15.2 mmole) in concentrated aqueous ammonia (300 mL) was stirred rapidly at ambient temperature (ca. 25° C.) for four days. Some suspension had adhered to the sides of the flask so some additional concentrated aqueous ammonia (50 mL) was used to wash down the sides of the flask followed by refluxing the mixture for 6.5 hours before cooling to ambient temperature again. Stirring was stopped, filtered, and the filtrate extracted three times with chloroform. The combined extracts were washed with cold saturated aqueous sodium chloride solution then cold water (100 mL each). The chloroform phase was dried over anhydrous sodium sulfate, filtered, then concentrated in vacuo to provide the desired material.

Route 2. A suspension of 1,5-bis-(4'-carbomethoxyphenyl)-3-pentanone (10.8 g, 30 mmole) in concentrated aqueous ammonia (600 mL) was charged to an autoclave and heated to 175° C. for 14 hours with good stirring. The suspension was cooled, THF added, and the phases separated. Both phases were concentrated in vacuo to provide 12.9 grams of slightly wet solids from the aqueous phase (FDMS confirms product) and 1.0 grams of solids from the organic phase (FDMS confirms desired product to be major material; some impurities exist, but are relatively low in concentration).

Example 4

1,5-Bis-(4'-aminomethylphenyl)-3-aminopentane (4)

To a 1-L round-bottom flask equipped with a magnetic stir-bar was added lithium aluminum hydride (95 percent powder, 9.2 grams) and THF (250 mL). Efficient stirring was initiated followed by the gradual addition of the damp 1,5-bis-(4'-carboxamidephenyl)-3-iminopentane (7.50 grams) prepared by route 2 above. The mixture was then heated to reflux and held there 10 hours before cooling and the careful quenching with water (18 mL), then 50 percent aqueous sodium hydroxide solution (64 grams), then again with water (18 mL). After stirring an additional hour, the solids were filtered. The filtrate was then concentrated in vacuo.

Example 5

1,5-Bis-(4'-aminomethylcyclohexyl)-3-aminopentane (5)

This reaction involves the direct hydrogenation of the aromatic rings in 1,5-bis-(4'-aminomethylphenyl)-3-aminopentane, 4, with a heterogeneous catalyst, such as, palladium on carbon.

Example 6

1,5-Bis-(4'-carbomethoxycyclohexyl)-3-pentanol (6) and 1,5-Bis-(4'-carbomethoxycyclohexyl)-3-pentanone (7)

The procedures to obtain these materials by catalytic hydrogenation have been described earlier in U.S. Pat. No. 5,025,086.

Example 7

1,5-Bis-(4'-hydroxymethylcyclohexyl)-3-pentanol (8)

This reaction involves reductions of simple esters and keto-esters (compounds 6 and 7) by hydride reagents, such as, lithium aluminum hydride in high yields. Reductions by catalytic hydrogenations usually require higher temperatures and pressures of hydrogen compared to hydrogenations of aromatic rings and simple isolated olefins.

Example 8

1,5-Bis-(4'-carboxamidecyclohexyl)-3-iminopentane (9)

This reaction procedure necessary to prepare this product from 7 would follow the same procedure(s) as that for preparing 3 from 2.

Example 9

1,5-Bis-(4'-(bis-2-hydroxyethyl) carboxamidephenyl)-3-(bis-2-hydroxyethyl)amino-2-1pentene (10)

A mixture of diethanolamine (34.7 g, 0.33 mole) and 1,5-bis-(4'-carbomethoxyphenyl)-3-pentanone (35.52 g, 0.10 mole) was heated to ca. 1 90° C. for about thirteen hours during which more than 10 mL of condensate was removed via a Dean-Stark trap. FDMS analysis shows the presence of the desired material along with 1,5-bis-(4'-(bis-2hydroxyethyl)carboxamidephenyl)-3-pentanol (a recheck by FDMS showed the starting material to contain some 1,5-bis-(4'-carbomethoxyphenyl)-3-pentanol).

Example 10

1,5-Bis-(4'-(bis-2-hydroxyethyl) carboxamidephenyl)-3-(bis-2-hydroxyethyl) aminopentane (11)

The preparation of this material would require the hydrogenation of 10.

Example 11

1,5-Bis-(4'-(bis-2-hydroxyethyl) carboxamidecyclohexyl)-3-(bis-2-hydroxyethyl) aminopentane (12)

The preparation of this material would require the hydrogenation of 10 under conditions of higher pressures and temperatures compared to the preparation of 11.

Example 12

1,5-Bis-(4'-(bis-2-hydroxyethyl) carboxamidecyclohexyl)-3-(bis-2-hydroxyethyl) amino-2-pentene (13)

Preparation of this material from 7 would be similar to that of preparing 10 from 2 as described previously.

The invention has been described in detail with particular reference to preferred embodiments thereof, but it will be understood that variations and modifications may be effected within the spirit and scope of the invention.

What is claimed is:

1. The compound 1,5-bis-(4'-aminomethylcyclohexyl)-3-aminopentane.

2. A process for preparing the compound of claim 1 comprising steps of hydrogenation of 1,5-bis-(4'-carbomethoxyphenyl)-1,4-pentadien-3-one to 1,5-bis-(4'-carbomethoxycyclohexyl)-3-pentanone; addition of anhydrous or aqueous ammonia to form 1,5-bis-(4'-carboxamidecyclohexyl)-3-iminopentane; and reduction to form the compound of claim 1.

3. A process for preparing the compound of claim 1 comprising steps of catalytic hydrogenation of 1,5-bis-(4'-carbomethoxyphenyl)-1,4-pentadien-3-one to 1,5-bis-(4'-carbomethoxyphenyl)-3-pentanone; addition of anhydrous or aqueous ammonia to form 1,5-bis-(4'-carboxamidephenyl)-3-iminopentane; reduction to form 1,5-bis-(4'-aminomethylphenyl)-3-aminopentane; and further reduction to form the compound of claim 1.

4. A thermoset coating composition comprising the compound of claim 1 and a compound selected from the group consisting of polyfunctional monomeric, oligomeric, and/or polymeric anhydrides, esters, carboxylic acids, carbonates, isocyanates, epoxies, acetoacetates, and alkoxylated melamines.

5. The compound 1,5-bis-(4'-aminomethylphenyl)-3-aminopentane.

6. A process for preparing the compound of claim 5 comprising reduction of 1,5-bis-(4'-carboxamidephenyl)-3-iminopentane.

7. A thermoset coating composition comprising the compound of claim 5 and a compound selected from the group consisting of polyfunctional monomeric, oligomeric, and/or polymeric anhydrides, esters, carboxylic acids, carbonates, isocyanates, epoxies, acetoacetates, and alkoxylated melamines.

8. The compound 1,5-bis-(4'-hydroxymethylcyclohexyl)-3-pentanol.

9. A process for preparing the compound of claim 8 comprising reduction of 1,5-bis-(4'-carbomethoxycyclohexyl)-3-pentanol and 1,5-bis-(4'-carbomethoxycyclohexyl)-3-pentanone.

10. A thermoset polyester composition comprising the compound of claim 8 reacted with at least one compound selected from the group consisting of anyhdrides, esters and carboxylic acids.

11. A thermoset composition comprising the compound of claim 8 reacted with at least one compound selected from the group consisting of carbonates, acetoacetates, epoxys and isocyanates.

12. A thermoset melamine-formaldehyde composition comprising the compound of claim 8 reacted with alkoxylated melamines.

13. The compound 1,5-bis-(4'-(bis-2-hydroxyethyl) carboxamidephenyl)-3-(bis-2-hydroxyethyl)aminopentane.

14. A process for the preparing the compound of claim 13 comprising hydrogenation of 1,5-bis-(4'-(bis-2-hydroxyethyl)carboxamidephenyl)-3-(bis-2-hydroxyethyl) amino-2-pentene.

15. A thermoset composition comprising the compound of claim 13 reacted with at least one compound selected from the group consisting of carboxylic acids, isocyanates and epoxies.

16. The compound 1,5-bis-(4'-(bis-2-hydroxyethyl) carboxamidecyclohexyl)-3-(bis-2-hydroxyethyl) aminopentane.

17. A process for preparing the compound of claim 16 comprising hydrogenation of 1,5-Bis-(4'-(bis-2-hydroxyethyl)carboxamidephenyl)-3-(bis-2-hydroxyethyl) amino-2-pentene under conditions of high temperature and pressure.

18. A thermoset composition comprising the compound of claim 16 reacted with at least one compound selected from the group consisting of carboxylic acids, isocyanates and epoxies.

* * * * *